United States Patent [19]

Barany et al.

[11] Patent Number: 5,545,698
[45] Date of Patent: Aug. 13, 1996

[54] POLYETHYLENE GLYCOL DERIVATIVES FOR SOLID-PHASE APPLICATIONS

[75] Inventors: George Barany, Falcon Heights, Minn.; Fernando Albericio, Barcelona, Spain; Nuria A. Solé, Boston, Mass.; Jane Chang, Buffalo Grove, Ill.; Samuel Zalipsky, Fremont, Calif.

[73] Assignee: University of Minnesota, Minneapolis, Minn.

[21] Appl. No.: 150,414

[22] Filed: Nov. 10, 1993

Related U.S. Application Data

[60] Continuation-in-part of Ser. No. 59,626, May 19, 1993, abandoned, which is a division of Ser. No. 760,768, Sep. 16, 1991, Pat. No. 5,235,028, which is a continuation-in-part of Ser. No. 715,289, Jun. 14, 1991, abandoned, which is a continuation-in-part of Ser. No. 576,314, Aug. 31, 1990, abandoned.

[30] Foreign Application Priority Data

Aug. 27, 1991 [WO] WIPO ............... PCT/US91/06103

[51] Int. Cl.$^6$ .................. C08F 8/32; C08G 69/26
[52] U.S. Cl. ............ 525/420; 525/374; 525/379; 525/382; 525/385; 525/386; 528/335; 530/334; 530/337
[58] Field of Search ................. 528/335; 525/420, 525/329.5; 530/334, 337

[56] References Cited

U.S. PATENT DOCUMENTS

| 4,115,361 | 9/1978 | Schulze et al. | 528/111 |
|---|---|---|---|
| 4,229,567 | 10/1980 | Sharkey | 528/338 |
| 4,282,346 | 8/1981 | Sharkey | 528/338 |
| 4,581,040 | 4/1986 | Sung et al. | 44/71 |
| 4,740,582 | 4/1988 | Coquard et al. | 528/339 |
| 4,789,721 | 12/1988 | Waddill et al. | 528/111 |
| 4,810,261 | 3/1989 | Sung et al. | 44/62 |
| 4,865,622 | 9/1989 | Sung | 44/63 |
| 4,929,716 | 5/1990 | Tyrell et al. | 528/353 |
| 4,946,933 | 8/1990 | Speranza et al. | 528/339.3 |

FOREIGN PATENT DOCUMENTS

| 0187391 | 12/1985 | European Pat. Off. |
|---|---|---|
| 3500180 | 1/1985 | Germany . |
| WO92/04384 | 3/1992 | WIPO . |

OTHER PUBLICATIONS

Hellerman et al., *Makromol. Chem.*, 184:2603–2617 (1983).
G. Odian, "Principles of Polymerization", 3d, 731–736 (1991) Wiley (New York).
M. Tomoi et al., "Synthesis and Phase-Transfer Catalytic Activity of Polymer-Supported Poly(ethylene Glycol)s,", Reactive Polymers, 10:27–36 (1989).
Pillai et al., "Synthesis of Thioredoxin Partial Sequences on a Polyethylenglycol–Grafted Polystyrene Support with a Photolytically Detachable 2–Nitrobenzyl Anchoring Group, " Chem. Abstract vol. 114:247733r (June 24, 1991).
S, Zalipsky et al., "Facile Synthesis of α–Hydroxy–w–Carboxymethylpolethlene Oxide, " J. Bioactive & Compat. Polymers, 5:227–231 (1990).
Barany and Albericio, "Mild Orthogonal Solid–Phase Peptide Synthesis. "In Peptides 1990, Giralt and Andreu (Eds.), ESCOM Science Publishers B.V., pp. 139–142 (1990).
Barany et al., "Biopolymer Syntheses on Novel Polyethylene Glycol–Polystyrene (PEG–PS) Graft Supports. "In Peptides, Smith and River (Eds.) ESCOM, Proceedings of the Twelfth American Peptides Symposium, Jun. 16–21, 1991, Cambridge, MA.
Barany et al., "Peptide Synthesis on Novel Polyethyleneglycol–Polystyrene (PEG–PS) Graft Supports, " Milligen/Biosearch Forum, Sep. 6, 1990.
Odigan, G., "Principles of Polymerization, " Third Edition, 731–736 (1991), Wiley (New York).
Haridasan, V.K., et al., "Synthesis of Substance P Partial Sequential Peptides on a Photolytically Removable 4–Aminomethyl–3–nitrobenzolaminomethyl Polystyrene Support, " Chem. Abstract vol. 114:247769g (Jun. 24, 1991).
W. M. McKenzie et al., " Polymer–supported Phase Transfer Catalysts in Solid–Liquid Reactions, " J. Chem. Soc. Chem. Commun., pp. 541–543 (1978).
S. L. Regen et al., "Solid–Phase Cosolvents. Triphase Catalytic Hydrolysis of 1–Bromoadamantane, " J. Amer. Chem. Soc., 101(1):116–120 (Jan. 3, 1979).
J. G. Heffernan et al., "Non–supported and Resin–supported Oligo (oxyethylenes) as Solid–Liquid Phase–transfer Catalysts. Effect of Chain Length and Head–group, " J. Chem. Soc. Perkin II, pp. 514–517 (1981).
H. Becker et al., "Polyethylenglycols Grafted Onto Crosslinked Polystyrenes: A new Class of Hydrophilic Polymeric Supports for Peptide Synthesis, " Makromol. Chem., Rapid Commun., 3:217–223 (1982).
E. Bayer et al., "Immobolized Polyoxyethlene, A New Support For Peptide Synthesis. " In Peptides: Structure and Function, Hruby and Rich (Eds.), Proc. 8th Am. Peptide Symp. pp. 87–90, Pierce Chem. Co., Rockford, IL (1983).
H. Hellermann et al., "Poly (etylene glycol)s Grafted Onto Crosslinked Polystyrenes, 2 [a)], Multidetachably Anchored Polymer Systems for the Synthesis of Solubilized Peptides, " Makromol. Chem., 184:2603–2617 (1983).
Y. Kimura et al., "Poly(ethylene glycol) –Grafted Copolymers as Synthetic Equivalents of Benzyltriethylammonium Chloride for Triphase Catalytic Alkylation [1], " J. Org. Chem., 48:385–386 (1983).
Zalipsky et al. "Preparation and Use of an Aminoethyl Polyethylene Glycol–Crosslinked Polystyrene Graft Resin Support for Solid–Phase Peptide Synthesis [1], " In Peptides: Structure and Function, Deber et al., (Eds. ), Proc. 9th Amer. Pep. Symp., pp. 257–260 Pierce Chem. Co., Rockford, IL (1985).
Bayer and Rapp, Abstract from World Patent Index (1986).

*Primary Examiner*—Fred Zitomer

[57] ABSTRACT

The present invention pertains to polyethylene glycol (PEG) derivatized graft supports, to methods for making these supports and to methods of using the supports to synthesize peptides by solid-phase synthesis techniques. The PEG-graft supports of this invention comprise functionalized PEG derivatives which are covalently attached to solid supports, such as polystyrene.

8 Claims, 4 Drawing Sheets

POLYETHYLENE GLYCOL DERIVATIVES FOR SOLID-PHASE APPLICATIONS

GOVERNMENT SUPPORT

Work described herein was supported in part by a grant from the National Institute of Health.

RELATED APPLICATION

This application is a continuation-in part application of U.S. patent application Ser. No. 08/059,626, filed May 10, 1993, now abandoned which is a divisional application of U.S. patent application Ser. No. 07/760,768, filed Sep. 16, 1991, now U.S. Pat. No. 5,235,028 which is a continuation-in-part application of U.S. patent application Ser. No. 07/715,289, filed Jun. 14, 1991, now abandoned, which is continuation-in-part application of U.S. patent application Ser. No. 07/576,314, filed Aug. 31, 1990, now abandoned, the entire teachings of which are incorporated herein by reference.

BACKGROUND OF THE INVENTION

Spacer arms are essential in many areas of modern biochemistry. Spacer arms can be defined as molecules which link one molecule to another molecule or to an inert support. Polyethylene glycol, for example, has been used advantageously to link enzymes to insoluble carriers and other biomolecules while retaining the activity of the enzyme. M. Stark and K. Holmberg, *Biotech. and Bioeng.*, 34:942–950 (1989). This concept has important consequences for industrial processes using immobilized enzymes (e.g., affinity column purification processes), and for diagnostic assays (e.g., ELISA assays). Two other areas in which polyethylene glycol spacer arms have been used are peptide synthesis and sequencing. The coupling rate of protected nucleotide and amino acid residues to inert supports, such as silica, membrane, and polystyrene supports, often increases commensurately with the separation of the reaction site from the support backbone. Similar effects have been shown for sequencing of solid-phase immobilized samples. J. K. Inman et al., In *Solid Phase Methods in Protein Sequence Analysis*, Previero and Coletti-Previero, (Eds.), Elsevier, North-Holland Biomed. Press, pp. 81–94 (1977).

The effectiveness of solid-phase nucleic acid or peptide synthesis or sequence analysis is affected by the solid-phase or support which anchors the reactive sites. Polystyrene gels or porous glass have both been utilized as solid supports for peptide sequencing, for example. In many applications, the solvents used in the process can cause the polystyrene particles to change in volume, which causes blocking of the reaction column and back pressure. Conversely, porous glass is completely rigid and does not change in volume, but the chemical properties of porous glass derivatives have lacked reproducibility. Polymer particles, such as polystyrene particles, which have been derivatized so that reactive groups can be attached to them, have proved useful In many applications. Polyethylene glycol (PEG) structures have been used as chemically inert spacer arms because they are compatible with a wide range of solvents. Inman et al., ibid. The use of PEG spacer arms minimizes the steric effects caused by the support. PEG spacer arms provide another useful function in modifying the character of the pore space so that the support-bound reactive moiety is compatible with a wider range of solvents and reagents.

PEG-modified polystyrene (PEG-PS) resins have been described for use in solid-phase peptide sequencing. Inman et al., ibid. PEG-PS resins have also been utilized as phase transfer catalysts. W. M. McKenzie et al., *J. Chem. Soc. Chem. Commun.*, p. 541–543 (1978); S. L. Regen et al., *J. Amer. Chem. Sot.*, 101:116–120 (1979); J. G. Heffernan et al., *J. Chem. Soc. Perkin II*, p. 514–517 (1981); Y. Kimura et al., *J. Org. Chem.*, 48:385–386 (1983); M. Tomoi et al., *Reactive Polymers*, 10:27–36 (1989). PEG-PS resins have been described as supports for solid-phase peptide synthesis. Becker et al., *Makromol. Chem. Rapid Commun.*, 3:217–223 (1982); H. Hellermann, et al., *Makromol. Chem.*, 184:2603–2617 (1983). However, PEG-PS resins prepared by the referenced methods suffer from several drawbacks. The reactions proceeded poorly with high molecular weight PEG (e.g., greater than 400 daltons) and symmetrical bifunctional PEG tended to form crosslinks. These problems were reduced by the anionic polymerization of ethylene oxide directly onto crosslinked polystyrene. Bayer et al., In *Peptides: Structure and Function*, V. J. Hruby and D. H. Rich (eds.), Proc. 8th Am. Peptide Symp. pp. 87–90, Pierce Chem. Co., Rockford, Ill. (1983). Bayer and Rapp, German Patent DE 3500180 A1 (1986). However, the PEG chain lengths are difficult to control using this method, and the uniformity of the PEG polymers is uncertain. Another problem with this process is that the polystyrene is functionalized using chloromethyl ether, which is highly toxic, and residual chloromethyl groups can cause side reactions during peptide synthesis.

Another method of making PEG graft copolymers is described by Zalipsky et al., In *Peptides:Structure and Function*, C. M. Deber, V. J. Hruby and K. D. Kopple (eds.), Proc. 9th Am. Pep. Syrup., pp. 257–260, Pierce Chem. Co., Rockford, Ill. (1985). In this method, certain heterobifunctional PEG derivatives of defined molecular weight (i.e., 2000 to 4000 daltons) were used. However, these derivatives are not readily available, which hinders their commercialization.

A method of preparing non-toxic and efficient solid supports which can be used with a wide range of solvents would be valuable for use in solid-phase synthesis or sequencing of peptides or nuclei acids, or for other solid-phase applications.

SUMMARY OF THE INVENTION

The present invention pertains to polyethylene glycol derivatized graft supports, to methods for making the supports, and to methods of using the supports to synthesize peptides by solid-phase synthesis techniques. The PEG-graft supports of this invention comprise functionalized PEG derivatives which are covalently attached to solid supports. In one embodiment, the PEG graft supports are represented by Formula I and shown in FIG. 1A:

Formula I

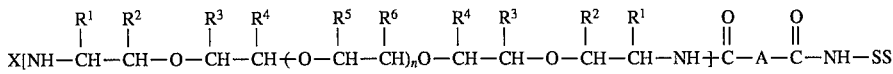

wherein n is an integer from about 5 to about 150; $R^1$, $R^2$, $R^3$, $R^4$, $R^5$ and $R^6$ are independently selected from the group consisting of hydrogen (H), and simple alkyl or aryl groups such as methyl, ethyl or phenyl; X is H or $H_2N$-B-NH-C(O)-A-C(O)-; and A and B are independently a straight chain or branched alkyl group, such as ethylene, propylene, isopropylene, butylene, isobutylene or other group up to about C-10 in length (e.g., A derived from succinic, glutaric, adipic or other such acids; B derived from ethylenediamine or other aliphatic diamines), a CH-CH group (e.g., A derived from maleic acid) or an aromatic group (e.g., A derived from phthalic acid; B derived from phenylenediamine). SS represents the solid support. The terminal amino group can optionally be protected by $N^\omega$ protecting groups, such as Boc, Fmoc and other known protecting groups. The core portion of the formula, indicated within the brackets, corresponds to a series of readily available amino-functionalized polyethylene glycol (PEG) polymer derivatives.

In another embodiment of the invention the resins are constructed such that peptide synthesis can occur at a point other than the terminus of PEG. Such resins are illustrated in FIG. 1B and further represented by the general Formula II:

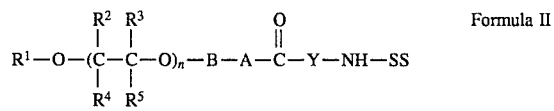

Formula II wherein Y is a diamino monocarboxylic acid that can optionally be protected by a $N^\omega$ protecting group; n is an integer from about 5 to about 150; SS is a solid support; B is a single bond or $-(CR^6R^7)_mN(H)C(O)-$ where m is 1 to 4, A is a straight chain or branched C1–C10 alkyl group, such as methylene, ethylene, propylone isopropylene, butylene and isobutylene; and $R^1$ to $R^7$ are independently selected from the group consisting of hydrogen, alkyl groups and aryl groups.

The present invention provides several compact, commercially viable routes for making functionalized inert supports for solid-phase applications using monofunctional or homobifunctional polyethylene glycol as the starting material. The present PEG graft supports provide advantageous physical and mechanical properties for solid-phase peptide synthesis, nucleic acid synthesis, and other applications where immobilized molecules are used.

DETAILED DESCRIPTION OF THE INVENTION

The present invention pertains to resins comprising a functionalized polyethylene glycol derivatives covalently linked to a solid support. In one embodiment, the resulting graft support comprises a symmetrical poly(oxyethylene) diamine derivative linked to the support and is represented by Formula I:

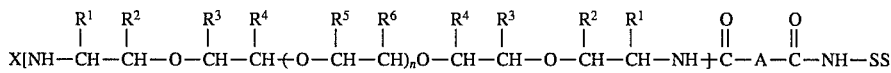

Formula I wherein n is an integer from 5 to about 150; $R^1$ $R^2$, $R^3$, $R^4$, $R^5$ and $R^6$ are independently selected from the group consisting of hydrogen (H), and simple alkyl or aryl groups such as methyl, ethyl or phenyl; SS is a solid support; X is H or $H_2N$-B-NH-C(O)-A-C(O)-; and A and B are independently a straight chain or branched alkyl group, such as ethylene, propylene, isopropylene, butylene, isobutylene or the like up to C-10 in length (e.g., A derived from succinic, glutaric, adipic or other such acids; B derived from ethylenediamine or other aliphatic aliamines); a CH-CH group (e.g., A derived from maleic acid) or an aromatic group (e.g., A derived from phthalic acid; B derived from phenylenediamine). The core portion of the formula, within the bracketed portion, corresponds to a series of polyoxyethylene diamine polymers. The amino group(s) can optionally be protected by known $N^\omega$ protecting groups.

Figure 2:
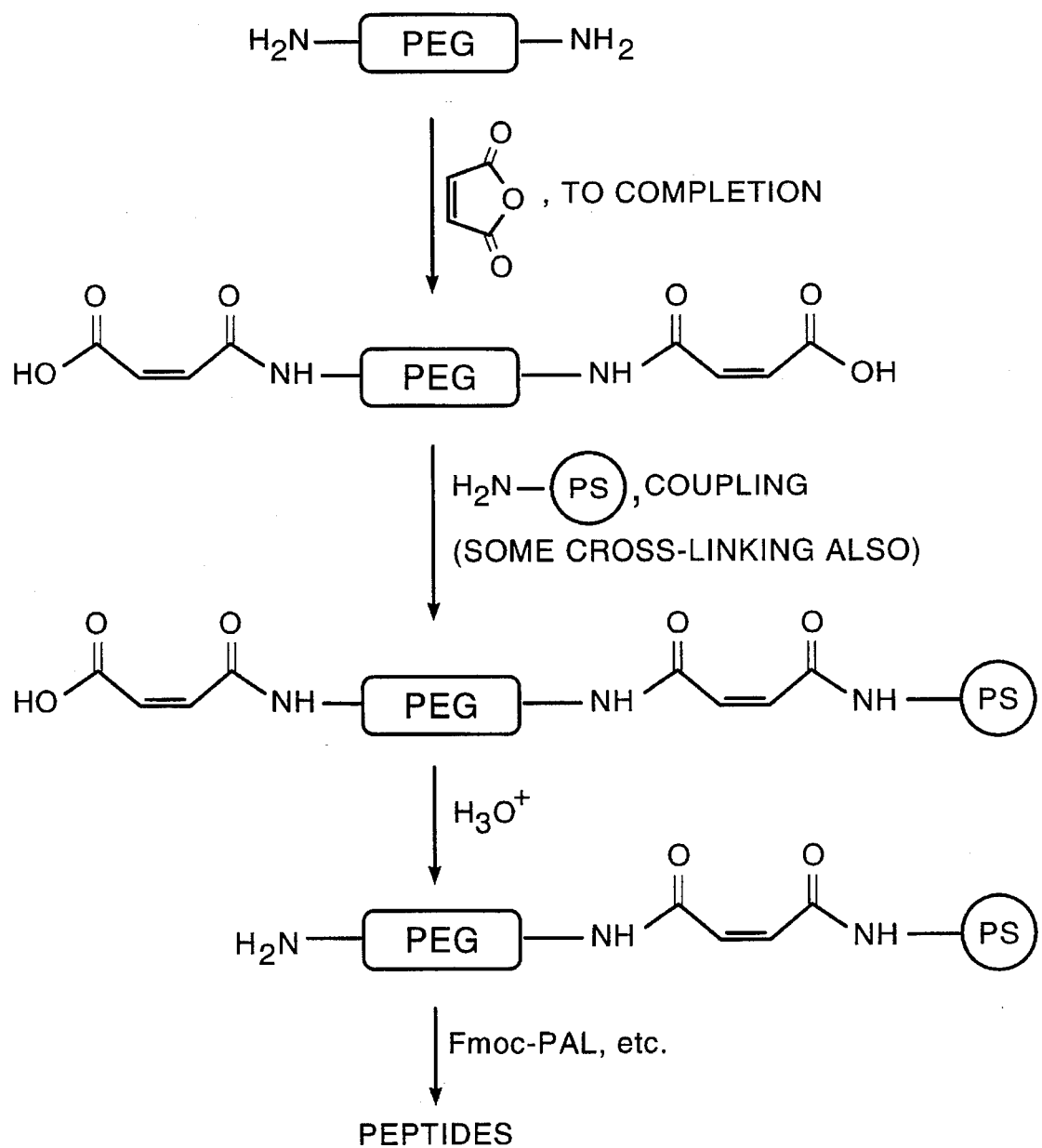
FIG. 2 is a schematic showing a series of reactions leading to preparation of a spacer arm linker, its coupling to an amino-functionalized polystyrene resin, attachment of a handle to the resin-bound linker, and its use to synthesize a peptide.
Figure 3:
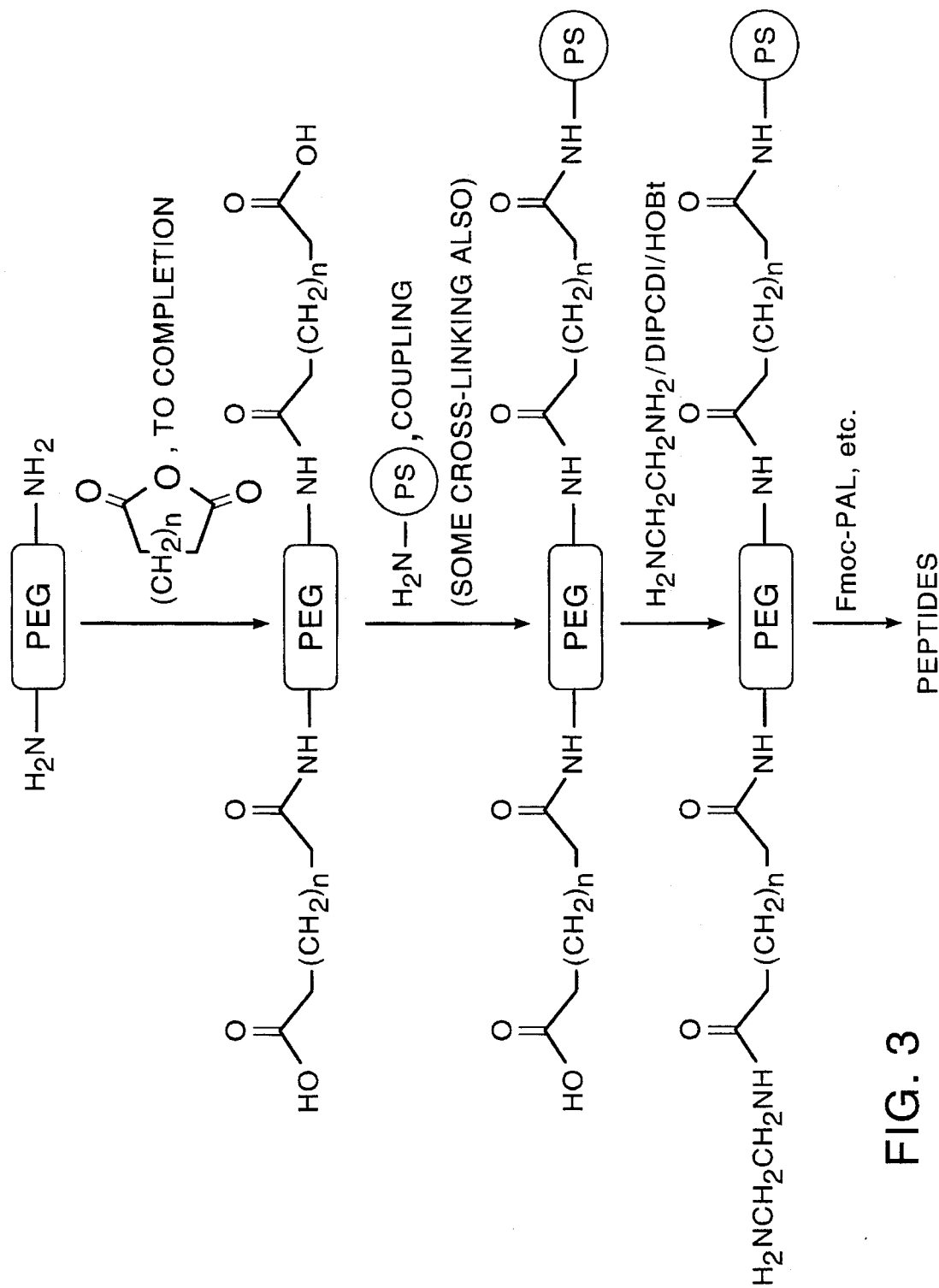
FIG. 3 is a schematic showing a series of reactions leading to further PEG-PS graft supports.

One method for producing the graft supports of Formula I is by reacting amino-functionalized core polymers with dicarboxylic acid derivatives, including anhydrides, to produce carboxyl-functional molecules. According to this method, the diamine polymer is reacted with at least two equivalents of the activated dicarboxylic acid derivative. Dicarboxylic acids which are useful in this method include alkyl diacids having up to about 12 carbon atoms, such as, for example, maleic, succinic, glutaric or adipic acid; anhydrides such as maleic, succinic or glutaric anhydride; or aromatic anhydrides, such as phthalic anhydride. In one embodiment of this method, the aliamine polymer is reacted with succinic, maleic or glutaric anhydride to make representatives of the claimed compounds, bis(succinylated), bis(maleylated) or bis(glutarylated) PEG. FIGS. 2 and 3 illustrate the formation and subsequent coupling of these derivatives onto an amino-functionalized solid support.

Homobifunctional PEG diamine compounds which can be subsequently reacted to produce resins of Formula I have the general Formula III:

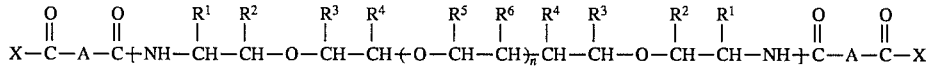

Formula III wherein n is an integer between about 5 and 150; $R^1$, $R^2$, $R^3$, $R^4$, $R^5$ and $R^6$ are independently selected from the group consisting of H, alkyl groups and aryl groups; X is selected from the group consisting of OH, halogens and the activating group of an active ester or thioester; and A is selected from the group consisting of straight chain or branched alkyl groups having up to about 10 carbon atoms, CH-CH groups and aromatic groups. The term "active ester" refers to compounds which activate carboxyl groups to make them undergo more ready reactions with amino groups. Activating groups which can be used in the present composition and method include, for example, trichlorophenyl (TCP) esters, pentafluorophenyl (PFP) esters, pentachlorophenyl (PCP) esters and methylphenylpyrazolinone (MPP) esters.

Symmetrical diamines which can be used as the core portion of the polymer include polymers corresponding to the bracketed portion of the structures shown in Formula I and Formula III. Such PEG derivatives having a theoretical content of amino groups can be obtained by a number of known processes. See, for example, Duckmann et al., *Makromol. Chem.*, 182:1379 (1983); Zalipsky et al., *Eur. Polym. J.*, 19:1177 (1983). Polymers which are particularly useful for this purpose include a series of poly(oxyethylene) diamines having a molecular weight up to about 6000 daltons which are commercially available under the tradename Jeffamine® (Texaco Chemical Co., Bellaire, Tex.). The Jeffamine® poly(oxyethylene) diamine resins are aliphatic primary diamines structurally derived from polypropylene oxide-capped polyethylene glycol. These products are characterized by high total and primary amine contents. Other symmetrical diamines having the desired characteristics can be used. For some applications, symmetrical dicarboxylic acid-functionalized polymers having approximately the same general structure can be used.

Carboxyl-functionalized spacer arm linkers produced by the present method are then coupled to appropriate parent carriers which have been functionalized with amino groups. Carriers which are useful as solid phases in the present invention include macromolecules or solids, such as membranes, porous glass, silica, polystyrenes, polydimethylacrylamides, cotton or paper. Solid supports which are particularly useful include amino-functionalized polystyrene, aminomethyl polystyrene, aminoacyl polystyrene and p-methylbenzhydrylamine polystyrene. A particularly preferred support is an amino-functionalized polystyrene-co-1% divinylbenzene. All amino groups of the parent carrier can be covered by reacting one equivalent of the carrier based on the amino groups with an excess of the carboxyl-functionalized derivatives. Most of the amino groups on the carrier become substituted by the polyethylene glycol derivatives, thereby forming spacer arms having one free pendant carboxyl group.

Introduction of an amino functionality on the present PEG derivatives is desirable for many synthesis applications. This can be achieved by acid hydrolysis (see FIG. 2) of the amide moiety, thereby exposing the amino group which was originally present on the diamine, or by further coupling of a free or monoprotected low molecular-weight diamine (e.g., ethylene or hexamethylene diamine) with the carboxylate end group (see FIG. 3). For parent carriers, modified by bis(maleylated) PEG linkers (see FIG. 2), for example, the terminal pendant maleyl group Is selectively hydrolyzed by controlled treatment with an acid, e.g., trifluoroacetic acid or dilute hydrochloric acid (HCl), whereas the other maleyl group, now linking the PEG to the carrier, is essentially stable. By these methods, amino-functionalized PEG-modified materials are obtained rapidly, efficiently and economically.

In another embodiment of the method of making PEG-PS graft co-polymers, the diacid or anhydride is first reacted with the amino-functionalized support, thereby forming an amide-linked carboxyl functionalized support. This carboxyl functionalized support is activated and then contacted with an excess of s bifunctional diamine polymer, represented by the core structure described above.

Figure 1A:
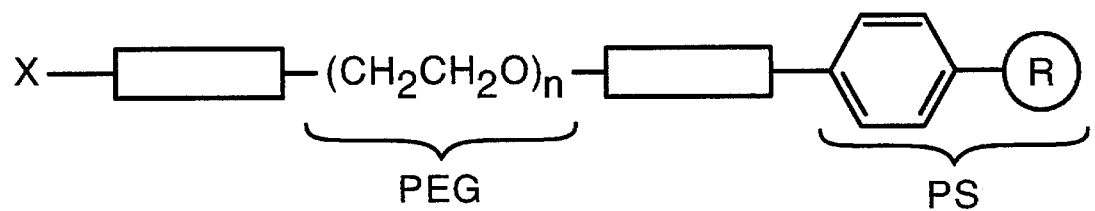
FIGS. 1A and 1B show the general structures of two types of polyethylene glycol-polystyrene (PEG-PS) graft supports. X illustrates the point from which biopolymer chain growth begins.
Figure 1B:
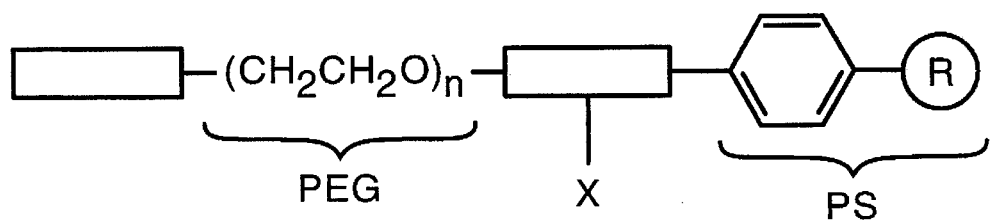

The PEG graft supports described above makes it possible to assemble biopolymers at the PEG terminus as shown in FIG. 1A. In another embodiment, however, the resins of the present invention can be constructed such that peptide synthesis can occur at a point other than the PEG terminus. Such resins are illustrated in FIG. 1B and are further represented by the general Formula II:

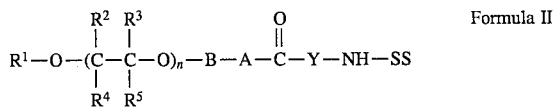

Formula II wherein Y is a diamino monocarboxylic acid that can optionally be protected by a $N^\omega$ protecting group; n is an integer from about 5 to about 150; SS is a solid support; B is a single bond or $-(CR^6R^7)_mN(H)C(O)-$ where m is 1 to 4, A is a straight chain or branched C1–C10 alkyl group, such as methylene, ethylene, propylene, isopropylene, butylene and isobutylene; and $R^1$ to $R^7$ are independently selected from the group consisting of hydrogen, alkyl groups and aryl groups.

A PEG graft support of this type (Formula II) is synthesized using a monofunctionalized polyethylene glycol (e.g., PEG monoamine or PEG monomethyl ether) which has been derivatized. Commercially available PEG starting materials are either monofunctional Jeffamine® or PEG memo methyl ether which has methoxy and hydroxyl end groups. An amino group on PEG can be reacted with a dicarboxylic acid or anhydride as already described. Alternatively, carboxyl-functionalized derivatives of MPEG can be made by reaction with ethyl bromoacetate, 4-bromovalerate or isocyanacetate, followed by saponification, for example as shown in the equation below.

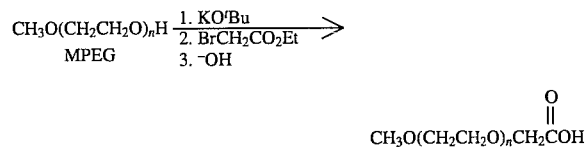

Figure 4:
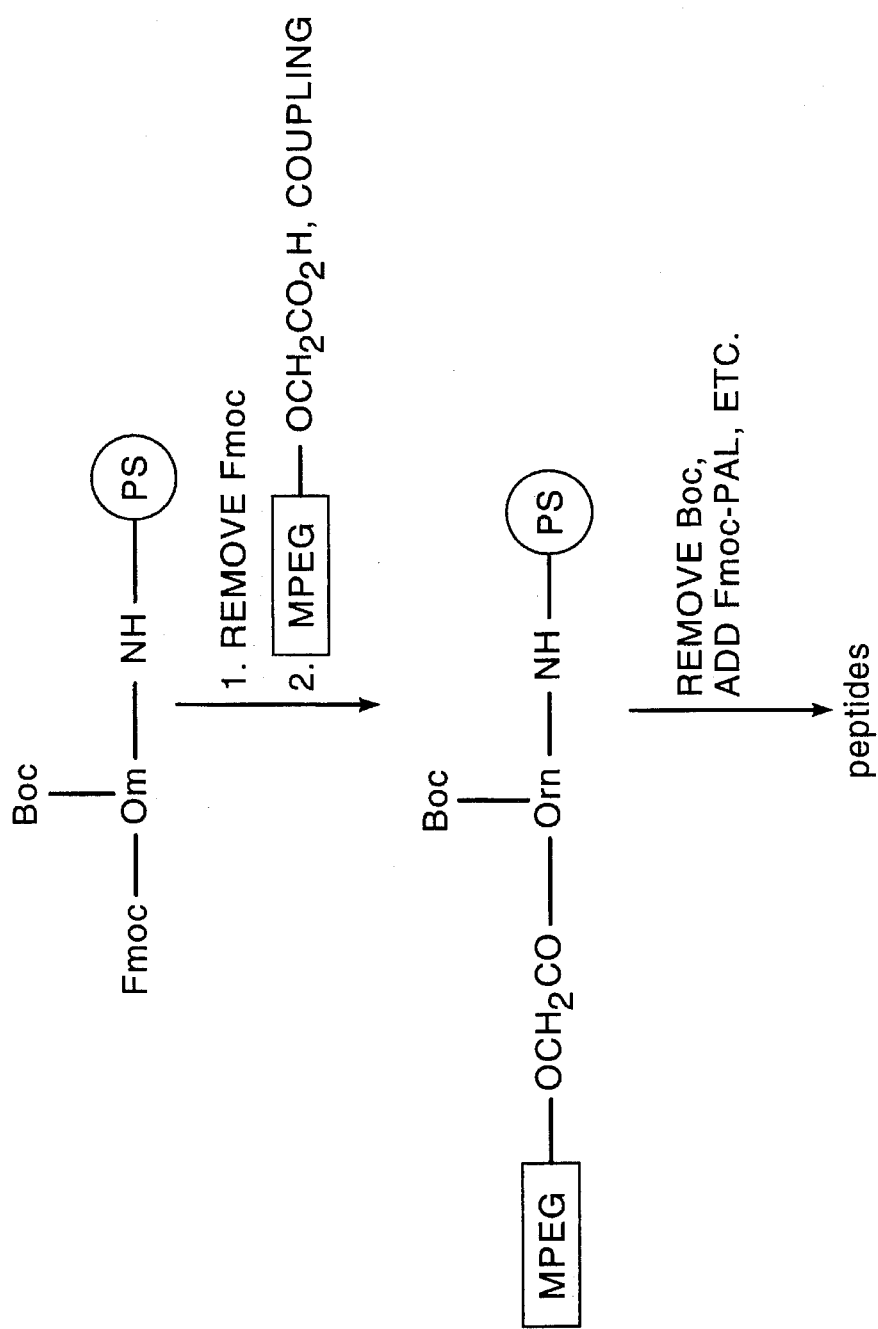
FIG. 4 is a schematic showing a series of reactions leading to a PEG-PS graft support in which the biopolymer can be synthesized from the Orn residue.

FIG. 4 schematically illustrates the synthesis of a PEG resin of Formula II. According to this method, an $N^\alpha$-Fmoc, $N^\delta$-Boc-Orn-PS resin (or a permutation on this theme) is aleblocked selectively, and a monofunctional PEG-acid is coupled on to form a branch orthogonal to the ultimate direction of biopolymer chain growth. An ornithine residue (as shown in FIG. 4) is used to link the PEG derivative to the solid support; however, other chemical moieties which have a carboxyl group and two amino groups can be used.

Polyethylene glycol-polystyrene (PEG-PS) graft supports made by the methods of this invention are particularly useful. PEG-PS supports made using the present PEG derivatives have several desirable characteristics for solid-phase applications: they swell in a variety of solvents, are stable under the condition used in most solid-phase synthesis, and behave well in both batch and column reactors used in solid-phase applications, in particular, solid-phase peptide synthesis.

Solid-phase peptide synthesis typically begins with covalent attachment of the carboxyl end of a first amino acid to the solid support. The carboxyl group of an $N^\alpha$-protected amino acid is covalently linked to a handle moiety which is attached to the amino group on the free end (the end not linked to the solid support) of the PEG spacer arm (FIGS. 1A, 2 and 3) or at a point other than the PEG terminus (FIGS. 1B and 4). A "handle" is defined as a bifunctional spacer which serves to attach the initial amino acid residue to the polymeric support. One end of the handle incorporates a smoothly clearable protecting group and the other end of the handle couples to the functionalized solid support. Handles which can be used with the present spacer arms in solid-phase peptide synthesis include, for example acid-labile p-alkoxybenzyl (PAB) handles, photolabtie o-nitrobenzyl ester handles, and handles such as those described by Albericio et al., *J. Org. Chem.*, 55:3730–3743 (1990) and references cited therein, and Din co-pending U.S. applications Ser. No. 07/576,233 now U.S. Pat. No. 5,196,566 by C. Barany and F. Albericio and Ser. No. 07/576,232 now U.S. Pat. No. 5,117,009 by C. Barany, both filed on Aug. 31, 1990, the teachings of all of which are hereby incorporated herein by reference. The appropriate handles are coupled quantitatively in a single step onto the amino-functionalized supports to provide a general starting point of well-defined structures for peptide chain assembly. The handle protecting group is removed and the C-terminal residue of the $N^\alpha$-protected first amino acid is coupled quantitatively to the handle. Once the handle is coupled to the solid-phase and the initial amino acid or peptide is attached to the handle, the general synthesis cycle proceeds. The synthesis cycle generally consists of deprotection of the $N^\alpha$-amino group of the amino acid or peptide on the resin, washing, and, if necessary, a neutralization step, followed by reaction with a carboxyl-activated form of the next $N^\alpha$-protected amino acid. The cycle is repeated to form the peptide or protein of Interest. Solid-phase peptide synthesis methods using functionalized insoluble supports are well known. Merrifield, *J. Am. Chem. Soc.*, 85:2149 (1963); Barany and Merrifield, In *Peptides*, Vol. 2, pp. 1–284 (1979); Barany et al., *Int. J. Peptide Protein Res.*, 30:705–739 (1987).

The present PEG-derivatives are particularly useful as spacer arms, which separate the theft support from the reacting amino acids which are forming the peptide chain during the synthesis process. The choice of a spacer arm, which provides this distance, is a critical parameter in solid-phase applications.

In a preferred embodiment of the present invention, a variety of PEG spacer arms having an average molecular weight of about 2000 daltons were incorporated between amino functional groups on a polystyrene backbone and the point for attachment of the appropriate handles. The resultant PEG-PS graft supports contained approximately equal weight amounts PEG and PS. These supports showed reproducible advantage over PS supports with regard to physical and chemical properties such as swelling and in synthesis of model peptides. The PEG-PS supports of this invention allow pep tide synthesis to be carried out using acetonitrile as the solvent for all reaction steps and washes. The control experiments using PS and employing acetonitrile as the solvent resulted in no peptide products.

In another embodiment, comparative experiments were carried out in which the difficult acyl carrier protein 65–74 decapeptide sequence was synthesized using Fmoc-amino acids. The peptide was produced in higher purity on this new PEG-PS than on either PS, Tentagel™ (a trademark of Rapp Chem., Tubingen, Germany), or Pepsyn K™ (a trademark of Cambridge Research Biochem., Cambridge, England). The PEG-PS material proved highly suitable both for flow-through synthesis and batch operation. Negligible back-pressures were found even at high flow rates.

The general usefulness of the PEG-PS graft support was demonstrated by syntheses of a number of large, (e.g., having about 30 to 60 residues) complex peptide sequences, such as cecropin analogues, calcitonin, β-endorphin, corticotropin releasing factor, two zinc finger binding sequences, and several partial sequences of HIV-1 tat protein. The improvements in synthetic efficiency which resulted from use of the present PEG-PS linkers appear to originate from one or more of the following: (i) a spacer arm effect removing the reaction sites from the vicinity of the polymer backbone; (ii) a general environmental effect which modifies the hydrophobic nature of the resin with a concomitantly favorable influence on reaction rates; and (iii) a specific effect on conformationally difficult couplings due to decreased secondary structure (hydrogen bond formation).

The. PEG derivatives can also be used in nucleic acid synthesis or sequencing as spacer arms or linkers between an inert support and the reacting nucleotide or nucleic acid. For example, the derivatives can be attached to polystyrene resins as described above and used in amidite-mediated DNA synthesis. The PEG-PS resin swells in acetonitrile, which is used as a solvent in the amidite coupling method.

The invention will now be further illustrated by the following examples:

EXAMPLES

Example 1

Preparation of a Bis(maleylated) Derivative of Jeffamine® ED-2001

Maleic anhydride (4.5 g, 46 mmol) was added in one portion to a stirred solution of Jeffamine® ED-2001 (30 g, 15 mmol, 30 mmol amino functions) in tetrahydrofuran (90 mL) at 25° C. After 5 hours, the solvent was removed by evaporation in vacuo, and the resulting oil was added to cold stirred ether (100 mL) at 0° C. over 5 minutes. The resulting white suspension was stirred at 0° C. for another 15 minutes, then collected by filtration, rinsed thoroughly with ether, and dried over phosphorus pentoxide in vacuo. Yield: 28.9 g (88%). NHR data and elemental analysis were in accord with the expected structure shown below:

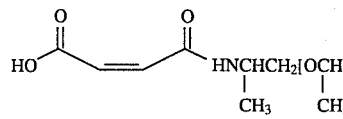 HNCHCH$_2$[OCHCH$_2$]$_a$ ⎯ [OCH$_2$CH$_2$]$_{40.5}$[OCH$_2$CH]$_b$NH 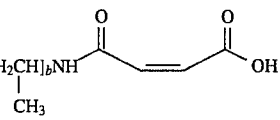
         |              |                                    |
        CH$_3$          CH$_3$                              CH$_3$ wherein a+b=2.5.

Example 2

Preparation of a Bis(gutarylated) Derivative of Jeffamine® ED-2001

A mixture of Jeffamine® ED-2001 (40 g, 20 mmol, 40 mmol amino functions) plus glutaric arthydride (5.0 g, 44 mmol) in dichloromethane (200 mL) was stirred at 25° C.

for 2 hours. The homogeneous reaction mixture, which gave a negative ninhydrin test indicating complete acylation, was concentrated in vacuo to provide a viscous oil which was decanted with vigorous stirring into a beaker containing ethyl ether (300 mL) at 4° C. A white precipitate formed quickly, which was collected, washed with further cold ether, and dried over phosphorus pentoxide in vacuo. Yield: 38 g (86%). NMR data and elemental analysis in accord with structure.

Example 3

Preparation of a Carboxymethyl Derivative of Polyethylene Glycol Methyl Ether A solution of polyethylene glycol methyl ether (MPEG), $M_w$ 2000 (100 g, 50 mmol) in toluene (500 mL) was refluxed overnight for azeotropic drying, with water removed by a Dean-Stark trap attachment. The solution was cooled to 80° C., treated with potassium tert-butoxide (11.2 g, 0.1 mol), and then a mixture of ethyl bromoacetate (11 mL, 0.1 mol) and toluene (10 mL) was added over 30 minutes. Reaction continued for 8 hours at 90° C., following which the mixture was concentrated in a rotary evaporator to for a brown viscous melt. Dichloromethane (500 mL) was added to extract the polymer, and activated alumina (200 g) was added. After 30 minutes, the organic phase was collected upon filtration, partially concentrated (to ~100 mL), combined with ethyl ether (700 mL), and brought to −20° C. for several hours. The precipitated polymer was collected by filtration, air-dried, and taken up in aqueous sodium hydroxide (1 N, 500 mL) for 3 hours, 25° C. This saponification reaction was quenched by acidification to pH 3 with concentrated aqueous HCl, and the product was extracted into dichloromethane mL). The organic phase was dried ($MgSO_4$), partially concentrated (to ~100 mL), combined with ethyl ether (700 mL), and brought to −20° C. for several hours. The final product was collected by filtration, and dried in vacuo over $P_2O_5$ for several days. Yield: 75 g (73%), titration of carboxyl groups 94% of theory. NMR data and elemental analysis in accord with structure.

Example 4

Procedure for Coupling- PEG-Diacid Derivative to MBHA-Resin

To a stirred solution of the PEG-diacid produced in Example 1, (26 g, 11.8 mmol, 23.6 mmol carboxyl groups), in N,N-dimethylformamide (DMF) (30 mL), was added 1-hydroxybenzotriazole (HOBt; 0.81 g, 6.0 mmol) in DMF (3 mL) and benzotriazol-1-yl-oxy-tris-(dimethylamino)-phosphonium hexafluorophosphate (BOP; 2.63 g, 6.0 mmol) in DMF (8 mL). A solution of N,N-diisopropylethylamtne (DIEA; 1.56 mL, 9 mmol) in dichloromethane (5 mL) was added over 10 minutes and the resulting solution stirred for another 10 minutes before transfer to a reaction vessel containing prewashed p-methylbeni-hydrylamine (MBHA) polystyrene resin support (5.0 g, 0.6 mmol/g, 3.0 mmol amino groups). The mixture was shaken for 2 days, until a ninhydrin test on a sample was almost negative. Unreacted amino groups were capped by acetylation, and the support was then washed with dichloromethane for further treatment, as described in Example 7.

Example 5

Procedure for Coupling PEG-Diacid Derivative to Nle-Resin

In a separate experiment, an aminomethyl polystyrene resin support (0.68 mmol/g) was derivatized with Fmoc-norleucine by standard procedures. A portion of the resultant Fmoc-Nle-resin (0.23 g, 0.55 mmol/g, 0.13 mmol) was deprotected with piperidine-DMF (3:7, v/v) (2+10 min) and washed with DMF and dichloromethane. In the meanwhile, the PEG-diacid from Example 2 (0.86 g, 0.39 mmol, 0.78 mmol carboxyl groups), BOP (88 mg, 0.2 mmol) and HOBt (27 mg, 0.2 mmol) were dissolved in DMF (4 mL), and then a solution of DIEA (45 μL, 0.26 mmol) in dichloromethane (2 mL) was added. After a 10 min preactivation period at 25° C., the PEG solution was added to the deprotected and washed resin, and coupling was carried out at 25° C. for 5 hours to give an essentially negative ninhydrin test. Capping was performed by the addition of acetic anhydride (40 μL, 0.4 mmol) in dichloromethane (2 mL) for 30 min. The final PEG-PS graft support (0.49 g) comprised PEG:PS:Nle-0.51:0.45:0.04 based on elemental analysis and amino acid analysis, from which it can be calculated that about 40% of the PEG chains were involved in cross-linking.

Example 6

Preparation of PEG-Orn(Boc)-PS Resin

An aminomethyl polystyrene resin support (6.0 g, 0.95 mmol/g, 5.7 mmol) was derivatized with $N^\alpha$-Fmoc, $N^\delta$-Boc-ornithine by standard procedures. The resin was swollen and washed with dichloromethane, neutralized with 5% DIEA in dichloromethane (1×5 min+3×10 min), and washed with dichloromethane. Coupling of the Orn derivative was mediated by N,N'-diisopropylcarbodiimide (DIPCDI)/HOBt in DMF method (3 equiv. each, 15 min preactivation, 40 mL reaction volume), 3 hours. Washing followed vtth DMF and dichloromethane. A ninhydrin test on a sample was nearly negative, but unreacted sites were blocked by capping with acetic anhydride (4.5 mL, 5 equiv.) and triethylamine (7.0 mL, 5 equiv.) in DMF (20 mL), 30 minutes. The protected Orn-PS resin (0.78 mmol/g, matches theoretical loading as adjusted for expected weight gain) was washed with DMF, dichloromethane, and treated with piperidine-DMF (1:4, v/v) (2+10 min) to remove selectively the $N^\alpha$-Fmoc group. Further washings with DMF, dichloromethane, 2-propanol, and DMF-dichloromethane (3:7, v/v) prepared the resin for coupling of the MPEG-acid derivative, produced as described in Example 3. A solution of the MPEG-acid (37 g, 18 mmol) in DMF-dichloromethane (3:7 v/v, 75 mL) was combined with HOBt (2.75 g, 18 mmol) and DIPCDI (2.83 mL, 18 mmol) for 15 minutes, and was then added to the H-Orn(Boc)-PS resin. Coupling proceeded for 5 hours giving a slightly positive ninhydrin test. A second coupling with smaller amounts of MPEG-acid derivative and activating agents (9 mmol scale), and acetylation by already-described procedures followed. The final MPEG-Orn(Boc)-PS resin was washed with dichloromethane, DMF, dichloromethane and methanol, and dried in vacuo over $P_2O_5$ for 48 hours. There was obtained 16.9 g of resin (excellent agreement with theoretical weight gain) with a loading of 0.31 mmol/g, comprising PEG:PS:Orn=0.57:0.36:0.07 by weight (based on elemental analysis and amino acid analysis). Similar results were obtained when BOP/HOBt/NMM in DMF protocols were used for activation and coupling.

Example 7

Procedure for Removal of Terminal Maleyl Group

The PEG-functionalized support prepared in Example 4 was washed with trifluoroethanol on a sintered funnels and transferred to a stianized round bottom flask. A mixture of trifluoroethanol/trifluoroacetic acid/water (8:1:1, 50 mL) was added and the suspension was heated at reflux (oil bath temp. 100° C.) and stirred magnetically for 24 hours. The material was then washed with dichloromethane, 5% DIEA in dichloromethane and methanol, and dried in vacuo in P$_2$O$_5$. Amino group content was determined on an aliquot by picric acid titration, or by loading with an Fmoc-amino acid. The final PEG-PS comprises PEG:PS=0.45:0.55 and has a loading of 0.17 mmol/g (based on CHN elemental analysis and amino acid analysis); it can be calculated that about 65% of the PEG chains in this support are acting as a spacer with the remainder involved in crosslinking.

Example 8

Procedure for Ethylenediamine Addition

The PEG-PS support from Example 5 (0.4 g, 0.12 mmol original Nle sites) was washed with dichloromethane for initial swelling, then DIPCDI (94 μL, 0.6 mmol) and HOBt (81 mg, 0.6 mmol) in DMF (2 mL) were added to the resin for a 5 minute preactivation period. Ethylenediamine (40 μL, 0.6 mmol) in DMF (0.5 mL) was then added to the resin for a 5 hour reaction. Final washes with DMF, dichloromethane and methanol were performed. The resin (0.4 g; no weight change from this step) was dried in vacuo over P$_2$O$_5$, following which the usual loading measurements with Fmoc-Ala revealed a substitution level of 0.11 mmol/g, and an Ala:Nle ratio of 0.30 (consistent with earlier estimate of extent of cross-linking).

Example 9

Batchwise Peptide Synthesis with Polyethylene Glycol-Polystyrene Graft (PEG-PS)

PEG-PS was prepared according to the procedure set out in Examples 4 and 7, starting with 5 grams of p-methylbenzhydrylamine resin (with loading 0.6 mmol/g), and 8.7 gram of PEG-PS product was obtained (loading 0.17 mmol/g). A 2 gram portion of this PEG-PS was extended with the Fmoc-PAL [5'-(4"-(9-fluorenylmethyloxycarbonyl) aminoethyl-3,5-dimethoxyphenoxy)valeric acid] handle which was linked by the BOP+HOBt protocol (D. Hudson, (1987) *J. Org. Chem.*, 53:617–624) to give a totally functionalized ninhydrin negative product. A test peptide, acyl cartier protein 65–74, was synthesized using a Milligen/Biosearch model 9600 peptide synthesizer, with the standard BOP+ HOBt coupling programs (Milligen/Biosearch, Novato, Calif.). In consecutive runs, Pepsyn K™, normal polystyrene and Tentagel™ supports were also used to make the same sequence. The resulting peptides were analyzed by amine acid analysis (AAA), high performance liquid chromatography (HPLC) and fast atom bombardment (FAB) mass spectrometry. The results showed that synthesis using PEG-PS provided the product in the highest yield with superior purity.

Example 10

Continuous Flow Peptide Synthesis with Polyethylene Glycol-Polystyrene Graft (PEG-PS)

PEG-Orn(Boc)-PS prepared as described in Example 6 was treated with TFA-dichloromethane (1:1) (5+25 min) to remove selectively the N$^\delta$-Boc group. There followed washing with dichloromethane, neutralization with 5% DIEA in dichloromethane and dichloromethane. Similar to Example 9, an Fmoc-PAL handle was added, and a Milligen/Biosearch model 9050 peptide synthesizer was used with a DIPCDI+HOBt coupling protocol (0.05 M concentrations), to make the challenging deca-alanyl-valine sequence. In a consecutive run, a normal polystyrene support was used to make the same sequence. The purity of the peptide based on HPLC was 77% when PEG-PS was used, as compared to 53% when PS was used.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A resin for solid-phasepeptide synthesis represented by the general formula:

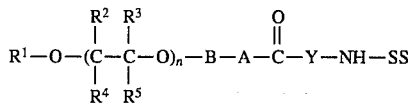

wherein Y is a diamino monocarboxylate moiety that optionally can be protected by an N$^\omega$ protecting group; n is an integer from about 5 to about 150; SS is a solid support; A is a straight chain or branched C1–C10 alkyl group; B is a single bond or -(CR$_6$R$_7$)$_m$- N(H)C(O)- where m is 1 to 4; and R$^1$ to R$^7$ are independently selected from the group consisting of hydrogen, alkyl groups and aryl groups.

2. The resin of claim 1 wherein the solid support is selected from the group consisting of amino-functional membranes, porous glass, silica, polystyrenes, polydimethylacrylamides, cotton and paper.

3. The resin of claim 2 wherein the solid support comprises a polystyrene selected from the group consisting of amino-polystyrene, aminomethyl polystyrene, aminoacyl polystyrene, benzhydrylamine polystyrene and p-methylbenzhydrylamine polystyrene.

4. A method of producing a resin for solid-phase peptide synthesis, comprising the steps of:

(a) coupling a bifunctional compound having a poly(oxyethylene) core and carboxyl end groups to an aminofunctionalized solid support under conditions sufficient for one of the carboxyl groups on the bifunctional compound to react with the amino groups on the solid support; and (b) introducing an amino functionality to replace the pendant terminal carboxyl group of the resin formed in step a.

5. The method of claim 4 wherein the bifunctional compound is produced by reacting amino groups on a poly(oxyethylene) diamine polymer with a dicarboxylic acid or an anhydride.

6. The method of claim 4 wherein the product of step (a) is represented by the general formula:

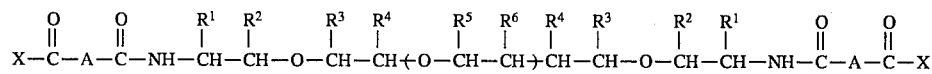

wherein n is an integer from about 5 to about 150; R$^1$, R$^2$, R$^3$, R$^4$, R$^5$ and R$^6$ are independently selected from the group consisting of H, alkyl groups and aryl groups; X is selected from the group consisting of OH, halogens, or the activating group of an active ester or thioester; and A is selected from the group consisting of straight chain or branched alkyl groups having up to about 10 carbon atoms, CH=CH groups and aromatic groups.

7. A method of producing a resin for solid-phase peptide synthesis, comprising the steps of:
   a) providing a solid support having attached thereto a diamino monocarboxylate having two $N^\omega$-amino protecting groups:
   b) removing a protecting group from one of the two $N^\omega$-amino moieties; and
   c) coupling a monofunctional carboxyl terminal polyethylene glycol derivative to the deprotected $N^\omega$-amino group to thereby produce the resin.

8. The method of claim 7 wherein the resin is represented by the formula:

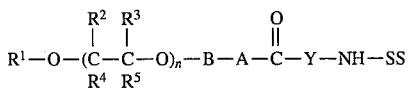

wherein Y is a diamino monocarboxylate moiety that optionally can be protected by a $N^\omega$ protecting group; n is an integer from about 5 to about 150; SS is a solid support; A is a straight chain or branched C1–C10 alkyl group; B is a single bond or $-(CR_6R_7)_m-N(H)C(O)-$ where m is 1 to 4; and $R^1$ to $R^7$ are independently selected from the group consisting of hydrogen, alkyl groups and aryl groups.

* * * * *